(12) United States Patent
Glue et al.

(10) Patent No.: US 6,524,570 B1
(45) Date of Patent: *Feb. 25, 2003

(54) POLYETHYLENE GLYCOL MODIFIED INTERFERON THERAPY

(75) Inventors: Paul Glue, Flemington, NJ (US); David L. Cutler, Morristown, NJ (US); Melton B. Affrime, Flemington, NJ (US)

(73) Assignee: Schering Corporation, Kanilworth, NJ (US)

(*) Notice: Subject to any disclaimer, the term of this patent is extended or adjusted under 35 U.S.C. 154(b) by 52 days.

This patent is subject to a terminal disclaimer.

(21) Appl. No.: 09/699,663

(22) Filed: Oct. 30, 2000

Related U.S. Application Data

(63) Continuation of application No. 09/281,401, filed on Mar. 30, 1999, now Pat. No. 6,177,074, which is a continuation of application No. 08/839,101, filed on Apr. 29, 1997, now Pat. No. 5,908,621, which is a continuation-in-part of application No. 08/742,305, filed on Nov. 1, 1996, now abandoned.

(60) Provisional application No. 60/006,130, filed on Nov. 2, 1995.

(51) Int. Cl.$^7$ .................... A61K 38/21; A61K 45/00; C07K 17/00; C12P 21/04

(52) U.S. Cl. .................... 424/85.7; 424/85.1; 530/351; 530/402; 435/69.51

(58) Field of Search ................ 424/85.7, 85.1; 435/69.51; 530/351, 402

(56) References Cited

U.S. PATENT DOCUMENTS

| | | | |
|---|---|---|---|
| RE29,835 E | 11/1978 | Witkowski et al. ............ 536/29 |
| 4,211,771 A | 7/1980 | Witkowski et al. .......... 424/180 |
| 4,530,901 A | 7/1985 | Weissmann .................. 435/70 |
| 4,791,192 A | 12/1988 | Nakagawa et al. .......... 530/399 |
| 4,985,253 A | 1/1991 | Fujioka et al. ............... 424/488 |
| 5,122,614 A | 6/1992 | Zalipsky ..................... 548/520 |
| 5,372,808 A | * 12/1994 | Blatt et al. |
| 5,382,657 A | 1/1995 | Karasiewicz et al. ....... 530/351 |
| 5,539,063 A | 7/1996 | Hakimi et al. .............. 525/403 |
| 5,559,213 A | 9/1996 | Hakimi et al. .............. 530/351 |
| 5,676,942 A | 10/1997 | Testa et al. ................. 424/857 |
| 5,711,944 A | * 1/1998 | Gilbert et al. |
| 5,767,097 A | 6/1998 | Tam ............................ 514/43 |
| 5,849,800 A | 12/1998 | Smith ........................ 514/647 |
| 5,908,621 A | 6/1999 | Glue et al. ................. 424/85.7 |
| 6,172,046 B1 | * 1/2001 | Albrecht ..................... 514/43 |
| 6,177,074 B1 | 1/2001 | Glue et al. ................. 424/85.7 |
| 6,299,872 B1 | * 10/2001 | Albrecht et al. ........... 424/85.7 |
| 6,387,365 B1 | * 5/2002 | Albrecht et al. ........... 424/85.4 |

FOREIGN PATENT DOCUMENTS

| | | |
|---|---|---|
| EP | 0 510 356 A1 | 3/1991 |
| EP | 0 593 868 A1 | 4/1994 |
| EP | 0 707 855 A2 | 4/1996 |
| EP | 0 809 996 A2 | 3/1997 |
| WO | WO 94/14474 | 7/1994 |
| WO | WO 95/13090 | 5/1995 |
| WO | WO 96/11953 | 4/1996 |
| WO | WO 96/36351 | 11/1996 |
| WO | WO 97/16204 | 5/1997 |
| WO | WO 97/18832 | 5/1997 |

OTHER PUBLICATIONS

Matsumura et al., Digestion, 1994, vol. 30, pp. 195–199.*
U.S. patent application Ser. No. 08/938,033, filed Sep. 21, 1997.
U.S. patent application Ser. No. 08/444,584, May 19, 1995.
U.S. patent application Ser. No. 08/742,305, filed Nov. 1, 1996.
Bizollon, T., et al. (1994), Revue Francaise De Castro–Enterologie, No. 297, vol. XXX, pp. 429 (English & French Language Versions).
Bizollon, T., et al. (1995), J. Hepatol., vol. 23 (Suppl. 2) pp. 22–25.
Bodenheimer, H.C., et al. (1994), Hepatology, vol. 20, No. 4, Pt. 2, Abstract No. 441.
Braconier, J.H., et al. (1995), Scan. J. Infect. Dis., vol. 27, pp. 325–329.
Brillanti, S., et al. (1993), Hepatology, vol. 18, pp. 150A (Abstract No. 375).
Brillanti, S., et al. (1993), J. Hepatol., vol. 18 (Suppl. 1), pp. S101 (Abstract No. T–69).
Brillanti, S., et al. (1994), Gastroenterology, vol. 107, pp. 812–817.
Brillanti, S., et al. (1995), J. Hepatol., vol. 23 (Suppl. 2), pp. 13–16.
Brouwer, J.T., et al. (1994), J. Hepatol., vol. 21 (Suppl. 1), pp. S17 (Abstract No. WP2/08).
Cavalletto, L., et al. (1993), Ital. J. Gastrenterol., vol. 25, Congress Proceedings (Venezia, Nov. 11–13, 1993), pp. 443–468 (Abstract at pp. 452).
Chemello, L., et al. (1994), J. Hepatol., vol. 21 (Suppl. 1), pp. S12 (Abstract No. GS 5/29).
Chemello, L., et al.. (1995), J. Hepatol., vol. 23 (Suppl. 2), pp. 8–12.
Cottrill, C.P., et al. (1997), Clinical Oncology, vol. 9, pp. 365–380.
Davis, G.L., et al. (1998), N. Engl. J. Med., vol. 339, pp. 1493–1492–1499.
Di Bisceglie, A.M., et al. (1992), Hepatology, vol. 16, pp. 649–654.
Fuertges, F., and Abuchowski, A. (1990), Journal of Controlled Release, vol. 11, pp. 139–148.

(List continued on next page.)

Primary Examiner—Yvonne Eyler
Assistant Examiner—Janet L. Andres
(74) Attorney, Agent, or Firm—Lerner, David, Littenberg, Krumholz & Mentlik, LLP

(57) ABSTRACT

A method comprising administering a $PEG_{12000}$-IFN alpha conjugate to an individual afflicted with a viral infection susceptible of treatment with interferon alpha, preferably chronic hepatitis C, is disclosed.

36 Claims, No Drawings

OTHER PUBLICATIONS

Hakozaki, Y., et al. (1995), Am. J. Gastroenterology, vol. 90(8), pp. 1246–1249.
Hoofnagle, J.H., et al. (1986), New Eng. J. Med., vol. 315, pp. 1575–1578.
Inada, Y., et al. (1995), TIBTECH, vol. 13, pp. 86–91.
Kakumu, S., et al. (1993), Gastroenterology, vol. 105, pp. 507–512.
Lai, M.Y., et al. (1993), Hepatology, vol. 18, pp. 93A (Abstract No. 146).
Lai, M.Y., et al. (1994), Symposium to the $9^{th}$ Biennial Scientific Mtg., Asian Pacific Assoc. for the Study of the Liver.
Lai, M.Y., et al. (1996), Gastroenterology, vol. 111, pp. 1307–1312.
Liang, T.J., et al. (1998), N. Engl. J. Med., vol. 339, pp. 1549–1550.
Main, J. (1995), J. Hepatol., vol. 23 (Suppl. 2), pp. 32–36.
Marcellin, P., et al. (1994), Baillere's Clin. Gastroenter., vol. 8, pp. 233–253.
McHutchinson, J.G., et al. (1998), N. Engl. J. Med., vol. 339, pp. 1485–1492.
The Merck Index, $11^{th}$ Ed., Compound No. 8199, pp. 1304.
Nieforth, K.A., et al. (1996), Clin. Pharmacol. Ther., vol. 59, pp. 636–646.
Northfelt, D.W., et al. (1995), Journal of Acquired Immune Deficiency Syndromes and Human Retrovirology, vol. 8, pp. 45–50.
Nucci, M.L., et al. (1991), Advanced Drug Delivery Reviews, vol. 6, pp. 133–151.
Poynard, T., et al. (1998), Lancet, vol. 352, pp. 1426–1432.
Reichard, O., et al. (1997), J. Hepatol., vol. 26 (Suppl. 1), pp. 1085–1115.
Reichard, O., et al. (1998), Lancet, vol. 351, pp. 83–87.
Sambataro, L. (1993), J. Hepatol., vol. 18 (Suppl. 1), pp. S167 (Abstract No. T–377).
Schvarcz, R., et al. (1995), J. Med. Virol., vol. 46, pp. 43–47.
Schvarcz, R., et al. (1995), J. Hepatol., vol. 23 (Suppl. 2), pp. 17–21.
Sherlock, S. (1995), J. Hepatol., vol. 23 (Suppl. 2), pp. 1–2.
Sherlock, S. (1995), J. Hepatol., vol. 23 (Suppl. 2), pp. 3–7.
Smith, D.B., et al. (1995), J. Hepatol., vol. 23 (Suppl. 2), pp. 26–31.
Telfer, P.T., et al. (1997), British J. Haemtatology, vol. 98, pp. 850–855.
Thomas, H., et al. (1994), Hepatology, vol. 20, No. 4, Pt. 2, Abstract No. 440.
Trepo, C., et al. (1994), Antiviral Res., vol. 24, pp. 155–163.
Wu, Z., et al. (1993), Antiviral Res. (Suppl. 1), Abstract No. 228.
Panel Discussion (1995), J. Hepatol., vol. 23 (Suppl. 2), pp. 37–40.
Package Insert for Intron A Interferon Alpha–2b Recombinant, 1992, Schering Corporation, Kenilworth, NJ.
Zauli, et al., Microbiologica, 1/93, 16(1):27–34.
Sandstrom, et al., Drugs 34(3):372–390 (9/87).
Roberts, et al., Clinical Pharmacology and Therapeutics, 42(4):365–373 (10/87).
Weiland, FEMS Microbiology Reviews 14(3):279–288 (7/94).
Berglund, et al. J. of Infectious Diseases, 163:710–715 (Apr. 1991).
Krown, et al., Annals of Internal Med, 112(11):812–821 (Jun. 1990).

* cited by examiner

POLYETHYLENE GLYCOL MODIFIED INTERFERON THERAPY

CROSS-REFERENCE TO RELATED APPLICATIONS

This application is a continuation of application Ser. No. 09/281,401, filed Mar. 30, 1999, now U.S. Pat. No. 6,177,074 B1, which is a continuation of application Ser. No. 08/839,101, filed Apr. 29, 1997, now U.S. Pat. No. 5,908,621, which is a continuation-in-part of application Ser. No. 08/742,305, filed Nov. 1, 1996, abandoned, which claim priority from provisional application Serial No. 60/006,130, filed Nov. 2, 1995, the disclosures of which are hereby incorporated in their entireties by reference.

This application is a continuation of application Ser. No. 09/281,401, filed Mar. 30, 1999, which is a continuation of application Ser. No. 08/839,101, filed Apr. 29, 1997, now U.S. Pat. No. 5,908,621, which is a continuation-in-part of application Ser. No. 08/1742,305, filed Nov. 1, 1996, abandoned, which claims priority from provisional application Serial No. 60/006,130, filed Nov. 2, 1995, the disclosures of which are hereby incorporated in their entireties by reference.

BACKGROUND OF THE INVENTION

The present invention relates to a method of treating viral infections, in particular, viral infections that are susceptible to treatment with interferon alpha, comprising the administration of an amount of a polyethylene glycol-interferon alpha conjugate, which amount is effective to treat the viral infection while reducing or eliminating adverse side effects normally associated with administration of interferon alpha. In a preferred embodiment of the invention, administration of a polyethylene glycol having an average molecular weight of 12,000 conjugated to interferon alpha is used to treat chronic hepatitis C.

Interferons are a family of naturally occurring small proteins and glycoproteins produced and secreted by most nucleated cells in response to viral infection as well as other antigenic stimuli. Interferons render cells resistant to viral infection and exhibit a wide variety of actions on cells. They exert their cellular activities by binding to specific membrane receptors on the cell surface. Once bound to the cell membrane, interferons initiate a complex sequence of intracellular events. In vitro studies demonstrated that these include the induction of certain enzymes, suppression of cell proliferation, immunomodulating activities such as enhancement of the phagocytic activity of macrophages and augmentation of the specific cytotoxicity of lymphocytes for target cells, and inhibition of virus replication in virus-infected cells.

Nonimmune interferons, which include both alpha and beta interferons, are known to suppress human immunodeficiency virus (HIV) in both acutely and chronically infected cells. Poli and Fauci, 1992, *AIDS Research and Human Retroviruses* 8(2):191–197. Interferons, in particular, alpha interferons, have received considerable attention as therapeutic agents in the treatment of hepatitis C virus (HCV)-related disease due to their antiviral activity. Hoofnagle et al., in: *Viral Hepatitis 1981 International Symposium*, 1982, Philadelphia, Franklin Institute Press; Hoofnagle et al., 1986, *New Eng. J. Med.* 315:1575–1578; Thomson, 1987, *Lancet* 1:539–541 Kiyosawa et al., 1983, in: Zuckerman, ed., *Viral Hepatitis and Liver Disease*, Allen K. Liss, New York pp. 895–897; Hoofnagle et al., 1985, *Sem. Liv. Dis.*, 1985, 9:259–263.

Chronic hepatitis C is an insidious and slowly progressive disease having a significant impact on the quality of life. Despite improvement in the quality of the blood-donor pool and the recent implementation of testing of donated blood for HCV, the estimated incidence of acute infection among persons receiving transfusions is 5 to 10%. Alter et al., in: Zuckerman, ed., *Viral Hepatitis and Liver Disease*, Allen K. Liss, New York, 1988, pp. 537–542. Thus, of the approximately 3 million persons who receive transfusions in the United States each year, acute hepatitis C will develop in about 150,000. While many patients who contract hepatitis C will have subclinical or mild disease, approximately 50% will progress to a chronic disease state characterized by fluctuating serum transaminase abnormalities and inflammatory lesions on liver biopsy. It is estimated that cirrhosis will develop in up to about 20% of this group. Koretz et al., 1985, *Gastroenterology* 88:1251–1254.

Interferons are known to affect a variety of cellular functions, including DNA replication and RNA and protein synthesis, in both normal and abnormal cells. Thus, cytotoxic effects of interferon are not restricted to tumor or virus infected cells but are also manifested in normal, healthy cells as well. As a result, undesirable side effects arise during interferon therapy, particularly when high doses are required. Administration of interferon can lead to myelosuppression resulting in reduced red blood cell, white blood cell and platelet levels. Higher doses of interferon commonly give rise to flu-like symptoms (e.g., fever, fatigue, headaches and chills), gastrointestinal disorders (e.g., anorexia, nausea and diarrhea), dizziness and coughing.

Interferon alpha-2b has been shown to be safe and effective when administered subcutaneously at a dose of $3 \times 10^6$ international units (IU) three times a week for 24 weeks for the treatment of chronic hepatitis C. Causse et al., 1991, *Gastroenterology* 101:497–502; Davis et al., 1989, *New Eng. J. Med.* 321:1501–1506; Marcellin et al., 1991, *Hepatology*, 13(3):393–393. This amount and duration alleviates symptoms of hepatitis C and biochemical or histological evidence of ongoing inflammation of the liver in some patients but it also causes undesirable side effects, e.g., flu-like symptoms. Thus, thrice weekly injections place a burden on the patient and have a significant impact on the patient's quality of life.

Nieforth et al. (Clin. Pharmacol. Ther., 1996, 59:636–646) has reported a comparison of the in vivo activity of ROFERON®A and a polyethylene glycol-modified ROFERON®A in healthy volunteers. The results, however, suggested that the conjugates could not be administered less than twice weekly and therefore offered little therapeutic advantage over the unmodified counterpart.

U.S. patent application Ser. No. 08/742,305 discloses methods of administering polymer-cytokine conjugates to individuals susceptible to treatment with the cytokine, but does not disclose the method of this invention.

Polyethylene glycol modification of other proteins has also been reported. See Fuertges et al., 1990, Journal of Controlled Release 11:139–48, which reports PEG-modified asparaginase for treatment of acute lymphoblastic leukemia, PEG-adenosine diaminase (PEG-ADA) for use in ADA-deficient Severe Combined Immunodeficiency Syndrome, PEG-superoxide dismutase for reperfusion injury and PEG-uricase for treatment of hyperuricemia.

The undesirable side effects that accompany interferon alpha therapy frequently limit the therapeutic usefulness of interferon alpha treatment regimes. Thus, a need exists to maintain or improve the therapeutic benefits of such therapy while reducing or eliminating the undesirable side effects.

SUMMARY OF THE INVENTION

The present invention fulfills this need by providing a method of treating conditions that are susceptible of treatment with interferon alpha, wherein efficacy is improved and undesirable side effects normally associated with such treatment are significantly diminished or eliminated entirely.

The present invention provides a method of treating a mammal afflicted with a viral infection that is susceptible to treatment with a interferon alpha comprising administering to the mammal an amount of a 12000 molecular weight polyethylene glycol conjugated interferon alpha ($PEG_{12000}$-interferon alpha), which amount is effective to treat the viral infection while substantially reducing or eliminating adverse side effects normally associated with administration of interferon alpha.

The present invention also provides a method of treating chronic hepatitis C virus infection comprising administering to a mammalian host infected with hepatitis C virus an amount of ($PEG_{12000}$-interferon alpha which is effective to treat said viral infection while simultaneously substantially reducing or eliminating side effects normally associated with administration of interferon alpha.

DETAILED DESCRIPTION OF THE INVENTION

The invention is directed to a method of treating conditions that are susceptible of treatment with interferon alpha. It has been unexpectedly discovered that administration of a 12000 molecular weight polyethylene glycol conjugated interferon alpha (hereinafter "$PEG_{12000}$-IFN") provides improved therapeutic benefits, while substantially reducing or eliminating entirely the undesirable side effects normally associated with conventionally practiced interferon alpha treatment regimes. In particular, it has surprisingly been found that administration once a week of a $PEG_{12000}$-IFN alpha-2b conjugate to patients with chronic hepatitis C results in equal or increased efficacy while substantially reducing or eliminating the side effects normally associated with conventionally practiced interferon alpha treatment regimes.

Conventional interferon alpha therapy used for treating HCV in humans is 3 million international units three times a week ("3 MIU TIW"). This therapy normally leads to myelosupression (reduction in white blood cells and neutrophil counts). Such doses or higher of interferon alpha commonly cause moderate to severe flu-like symptoms, gastrointestinal disorders, dizziness and coughing; each of these symptoms may require treatment with other therapies or force the patient to discontinue or reduce dosages of interferon alpha therapy.

Surprisingly, we have discovered that use of the preferred $PEG_{12000}$-IFN alpha-2b conjugates in accordance with the present invention allows higher and less frequent doses with higher efficacy while simultaneously and surprisingly substantially reducing or even eliminating the side effects and symptoms associated with conventional interferon alpha therapy.

The phrases "12,000 molecular weight polyethylene glycol conjugated interferon alpha" and "$PEG_{12000}$-IFN alpha" as used herein mean conjugates such as are prepared according to the methods of International Application No. WO 95/13090 and containing urethane linkages between the interferon alpha 2a or 2b amino groups and polyethylene glycol having an average molecular weight of 12000. The preferred polyethylene-glycolinterferon alpha conjugate is $PEG_{12000}$-interferon alpha-2b.

The preferred $PEG_{12000}$-interferon alpha-2b is prepared by attaching a PEG polymer to the epsilon amino group of a lysine residue in the IFN alpha-2b molecule. A single $PEG_{12000}$ molecule is conjugated to free amino groups on an IFN alpha-2b molecule via a urethane linkage. This conjugate is characterized by the molecular weight of $PEG_{12000}$ attached. The $PEG_{12000}$-IFN alpha conjugate is formulated as a lyophilized powder for injection. The objective of conjugation of IFN alpha with PEG is to improve the delivery of the protein by significantly prolonging its plasma half-life, and thereby provide protracted activity of IFN alpha.

The term "interferon" or "IFN" as used herein means the family of highly homologous species-specific proteins that inhibit viral replication and cellular proliferation and modulate immune response. Human interferons are grouped into three classes based on their cellular origin and antigenicity: α-interferon (leukocytes), β-interferon (fibroblasts) and γ-interferon (B cells). Recombinant forms of each group have been developed and are commercially available. Subtypes in each group are based on antigenic/structural characteristics. At least 24 interferon alphas (grouped into subtypes A through H) having distinct amino acid sequences have been identified by isolating and sequencing DNA encoding these peptides. The terms "α-interferon", "alpha interferon", "interferon alpha" and "human leukocyte interferon" are used interchangeably in this application to describe members of this group. Both naturally occurring and recombinant α-interferons, including consensus interferon, may be used in the practice of the invention.

The purification of interferon alpha from human leukocytes isolated from the buffy coat fraction of whole blood is described in U.S. Pat. No. 4,503,035. Human leukocyte interferon prepared in this manner contains a mixture of human leukocyte interferons having different amino acid sequences. Purified natural human α-interferons and mixtures thereof which may be used in the practice of the invention include but are not limited to SUMIFERON® interferon alfa-n1 available from Sumitomo, Japan, WELLFERON® interferon alfa-n1 (Ins) available from Glaxo-Wellcome Ltd., London, Great Britain, and ALFERON® interferon alfa-n3 available from the Purdue Frederick Co., Norwalk, Conn.

The advent of recombinant DNA technology applied to interferon production has permitted several human interferons to be successfully synthesized, thereby enabling the large-scale fermentation, production, isolation, and purification of various interferons to homogeneity. Recombinantly produced interferon retains its in vitro and in vivo antiviral and immunomodulatory activities. It is also understood that the recombinant techniques could also include a glycosylation site for addition of a carbohydrate moiety on the recombinantly-derived polypeptide.

The construction of recombinant DNA plasmids containing sequences encoding at least part of human leukocyte interferon and the expression in *E. coli* of a polypeptide having immunological or biological activity of human leukocyte interferon is disclosed in U.S. Pat. No. 4,530,901 and European Patent No. EP 0 032 134. The construction of hybrid α-interferon genes containing combinations of different subtype sequences (e.g., A and D, A and B, A and F) is disclosed in U.S. Pat. Nos. 4,414,150, 4,456,748 and 4,678,751. Typical suitable recombinant α-interferons which may be used in the practice of the invention include but are not limited to interferon alfa-2b such as INTRON®A available from Schering Corporation, Kenilworth, N.J., interferon alfa-2a such as ROFERON®A available from Hoffman-La Roche, Nutley, N.J.

U.S. Pat. Nos. 4,695,623 and 4,897,471 disclose human leukocyte interferon polypeptides, referred to as consensus interferon, which have amino acid sequences which include common or predominant amino acids found in each position among naturally-occurring interferon alpha subtype polypeptides.

Conditions that can be treated in accordance with the present invention are generally those that are susceptible to treatment with interferon alpha. For example, susceptible conditions include conditions which would respond positively or favorably as these terms are known in the medical arts to interferon alpha-based therapy. For purposes of the invention, conditions that can be treated with interferon alpha therapy include those conditions in which treatment with an interferon alpha shows some efficacy, but which may not be treatable with interferon alpha because the negative side effects outweigh the benefits of the treatment. For example, side effects accompanying alpha therapy have virtually ruled out treatment of Epstein Barr virus using interferon alpha. Practice of the invention results in substantially reduced or eliminated side effects as compared to conventional interferon alpha treatment.

Exemplary conditions which can be treated with interferon include but are not limited to cell proliferation disorders, in particular cancer (e.g., hairy cell leukemia, Kaposi's sarcoma, chronic myelogenous leukemia, multiple myeloma, basal cell carcinoma and malignant melanoma, ovarian cancer, cutaneous T cell lymphoma), and viral infections. Without limitation, treatment with interferon may be used to treat conditions which would benefit from inhibiting the replication of interferon-sensitive viruses. For example, interferon can be used alone or in combination with AZT in the treatment of HIV/AIDS or in combination with ribavirin in the treatment of HCV. Viral infections which may be treated in accordance with the invention include hepatitis A, hepatitis B, hepatitis C, other non-A/non-B hepatitis, herpes virus, Epstein-Barr virus (EBV), cytomegalovirus (CMV), herpes simplex, human herpes virus type 6 (HHV-6)), papilloma, poxvirus, picornavirus, adenovirus, rhinovirus, human T lymphotropic virus-type 1 and 2 (HTLV-1/-2), human rotavirus, rabies, retroviruses including human immunodeficiency virus (HIV), encephalitis and respiratory viral infections. The method of the invention can also be used to modify various immune responses.

Two variants of interferon alpha are currently approved in the United States and other countries for the treatment of hairy cell leukemia, venereal warts, Kaposi's Sarcoma, and chronic non-A/non-B hepatitis: interferon alfa-2b, marketed under the trade name INTRON® A (Schering Corporation, Kenilworth N.J.) and interferon alfa-2a, marketed under the trade name ROFERON® A (Hoffman-La Roche, Nutley, N.J.). Since interferon alpha-2b, among all interferons, has the broadest approval throughout the world for treating chronic hepatitis C infection, it is most preferred for use in the treatment of chronic hepatitis C in accordance with practice of the invention.

A person suffering from chronic hepatitis C infection may exhibit one or more of the following signs or symptoms: (a) elevated ALT, (b) positive test for anti-HCV antibodies, (c) presence of HCV as demonstrated by a positive test for HCV-RNA, (d) clinical stigmata of chronic liver disease, (e) hepatocellular damage. Such criteria may not only be used to diagnose hepatitis C, but can be used to evaluate a patient's response to drug treatment.

Elevated serum alanine aminotransferase (ALT) and aspartate aminotransferase (AST) are known to occur in uncontrolled hepatitis C, and a complete response to treatment is generally defined as the normalization of these serum enzymes, particularly ALT (Davis et al., 1989, New Eng. J. Med. 321:1501–1506). ALT is an enzyme released when liver cells are destroyed and is symptomatic of HCV infection. Interferon causes synthesis of the enzyme 2',5'-oligoadenylate synthetase (2'5'OAS), which in turn, results in the degradation of the viral mRNA. Houglum, 1983, Clinical Pharmacology 2:20–28. Increases in serum levels of the 2'5'OAS coincide with decrease in ALT levels.

Histological examination of liver biopsy samples may be used as a second criteria for evaluation. See, e.g., Knodell et al., 1981, *Hepatology* 1:431–435, whose Histological Activity Index (portal inflammation, piecemeal or bridging necrosis, lobular injury and fibrosis) provides a scoring method for disease activity.

In the practice of the invention, the preferred $PEG_{12000}$-IFN alpha-2a or -2b conjugates may be administered to patients infected with the hepatitis C virus. Use of $PEG_{12000}$-IFN alpha-2b is preferred.

Patients were selected for treatment from anti-HCV antibody patients with biopsy-documented chronic active hepatitis. Each patient was positive for antibody to hepatitis C virus (anti-HCV) by supplemental assay (Ortho or Abbot), had the presence of HCV RNA by PCR, and had previous liver biopsy with features of chronic hepatitis. Patients ranged from 18–68 years of age and had no previous interferon treatment for hepatitis C.

Three doses of $PEG_{12000}$-IFN alpha-2b (0.5, 1.0, 1.5 μg/kg) administered once a week were found to have equal to or better antiviral activity than the interferon alpha control 3 MIU TIW (measured by loss of HCV-RNA(PCR)) at 4, 8 and 12 weeks of therapy. At the same time, side effects known to accompany interferon alpha treatment were significantly diminished.

The amount of the $PEG_{12000}$-IFN alpha conjugate administered to treat any of the conditions described above is based on the IFN alpha activity of the polymeric conjugate. It is an amount that is sufficient to significantly affect a positive clinical response while maintaining diminished side effects. The amount of $PEG_{12000}$-IFN alpha-2b which may be administered is in the range of at least about 0.25 μg/kg in single or divided doses. In more preferred embodiments, the amount administered is in the range of about 0.25–2.5 μg/kg, or 0.5–1.5 μg/kg in single or divided doses.

Administration of the described dosages may be every other day, but is preferably once or twice a week. Doses are administered over at least a 24 week period by injection.

Administration of the dose can be intravenous, subcutaneous, intramuscular, or any other acceptable systemic method. Based on the judgment of the attending clinician, the amount of drug administered and the treatment regimen used will, of course, be dependent on the age, sex and medical history of the patient being treated, the neutrophil count (e.g. the severity of the neutropenia), the severity of the specific disease condition and the tolerance of the patient to the treatment as evidenced by local toxicity and by systemic side-effects. Dosage amount and frequency may be determined during initial screenings of neutrophil count.

For any route of administration, divided or single doses may be used. For example, when a subcutaneous injection is used to deliver, for example, 1.5 μg/kg of $PEG_{12000}$-IFN alpha-2b over one week, two injections of 0.75 μg/kg at 0 and 72 hours may be administered.

In order to follow the course of HCV replication in subjects in response to drug treatment, HCV RNA may be measured in serum samples by, for example, a nested polymerase chain reaction assay that uses two sets of primers derived from the NS3 and NS4 non-structural gene regions of the HCV genome. Farci et al., 1991, *New Eng. J. Med.* 325:98–104. Ulrich et al., 1990, *J. Clin. Invest.,* 86:1609–1614.

Antiviral activity may be measured by changes in HCV-RNA titre. HCV RNA data may be analyzed by comparing titres at the end of treatment with a pre-treatment baseline measurement. Reduction in HCV RNA by week 4 provides evidence of antiviral activity of a compound. Kleter et al., 1993, *Antimicrob. Agents Chemother.* 37(3):595–97; Orito et al., 1995, *J. Medical Virology,* 46:109–115. Changes of at least two orders of magnitude ($\geq 2$ log) is interpreted as evidence of antiviral activity.

Safety and tolerability may be determined by clinical evaluations and measure of white blood cell and neutrophil counts. This may be assessed through periodic monitoring of hematological parameters (white blood cell, neutrophil, platelet and red blood cell counts).

Other interferon conjugates can be prepared by coupling an interferon to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinyl pyrrolidones, polyacrylamides, polyvinyl alcohols, carbohydrate-based polymers and the like can be used. Such interferon-polymer conjugates are described in U.S. Pat. Nos. 4,766,106, 4,917,888, European Patent Application No. 0 236 987, European Patent Application No. 0 510 356 and International Application Publication No. WO 95/13090.

Since the polymeric modification sufficiently reduces antigenic responses, the foreign interferon need not be completely autologous. Interferon used to prepare polymer conjugates may be prepared from a mammalian extract, such as human, ruminant or bovine interferon, or recombinantly produced.

Various other extended- or sustained-release formulations can be prepared using conventional methods well known in the art.

Conventional pharmaceutical compositions comprising a therapeutically effective amount of $PEG_{12000}$-IFN alpha together with pharmaceutically acceptable carriers, adjuvants, diluents, preservatives and/or solubilizers may be used in the practice of the invention. Pharmaceutical compositions of interferon include diluents of various buffers (e.g., Tris-HCl, acetate, phosphate) having a range of pH and ionic strength, carriers (e.g., human serum albumin), solubilizers (e.g., tween, polysorbate), and preservatives (e.g., thimerosol, benzyl alcohol). See, for example, U.S. Pat. No. 4,496,537.

As described above, the course of the disease and its response to drug treatments may be followed by clinical examination and laboratory findings. The effectiveness of the therapy of the invention is determined by the extent to which the previously described signs and symptoms of chronic hepatitis are alleviated and the extent to which the normal side effects of interferon (i.e., flu-like symptoms such as fever, headache, chills, myalgia, fatigue, etc. and central nervous system related symptoms such as depression, paresthesia, impaired concentration, etc.) are eliminated or substantially reduced.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of treating a patient suspected of having hepatitis C infection, comprising administering to the patient a conjugate comprising polyethylene glycol (PEG) and an alpha interferon once per week in an amount effective to treat the infection.

2. The method of claim 1 wherein said interferon is interferon alpha-2a.

3. The method of claim 1 wherein said interferon is interferon alpha-2b.

4. The method of claim 1 wherein said interferon comprises consensus alpha interferon.

5. The method of claim 1 wherein said interferon comprises naturally occurring alpha interferon.

6. The method of claim 1 wherein said interferon comprises recombinant alpha interferon.

7. The method of claim 1 wherein the amount of the conjugate administered is 0.5 µg/kg.

8. The method of claim 1 wherein the amount of the conjugate administered is 2.0 µg/kg.

9. The method of claim 1 wherein the amount of the conjugate administered is 0.5, 1.0, or 1.5 µg/kg.

10. The method of claim 1 wherein said PEG is conjugated to said alpha interferon via an epsilon amino group of a lysine residue in said alpha interferon.

11. The method of claim 1 wherein said PEG is conjugated to free amino groups of said alpha interferon via a urethane linkage.

12. A method of treating a patient suspected of having hepatitis C infection, comprising administering to the patient a conjugate comprising polyethylene glycol (PEG) and an alpha interferon once or twice per week in an amount effective to treat the infection.

13. The method of claim 12 wherein said interferon is interferon alpha-2a.

14. The method of claim 12 wherein said interferon is interferon alpha-2b.

15. The method of claim 12 wherein said interferon comprises consensus alpha interferon.

16. The method of claim 12 wherein said interferon comprises naturally occurring alpha interferon.

17. The method of claim 12 wherein said interferon comprises recombinant alpha interferon.

18. The method of claim 12 wherein the amount of the conjugate administered is 0.5 µg/kg.

19. The method of claim 12 wherein the amount of the conjugate administered is 2.0 µg/kg.

20. The method of claim 12 wherein the amount of the conjugate administered is 0.5, 1.0, or 1.5 µg/kg.

21. The method of claim 12 wherein said PEG is conjugated via an epsilon amino group of a lysine residue in said interferon alpha.

22. The method of claim 12 wherein said PEG is conjugated to free amino groups of said interferon alpha via a urethane linkage.

23. The method of claim 12 wherein said conjugate is administered to said patient twice per week.

24. A method of treating a patient suspected of having hepatitis C infection, comprising administering to the patient in combination, ribavirin and a conjugate comprising polyethylene glycol (PEG) and an alpha-interferon, each in amounts effective to treat the infection, wherein the conjugate is administered once or twice per week.

25. The method of claim 24 wherein said interferon is interferon alpha-2a.

26. The method of claim 24 wherein said interferon is interferon alpha-2b.

27. The method of claim 24 wherein said interferon comprises consensus alpha interferon.

28. The method of claim 24 wherein said interferon comprises naturally occurring alpha interferon.

29. The method of claim 24 wherein said interferon comprises recombinant alpha interferon.

30. The method of claim 25 wherein the amount of the conjugate administered is 0.5 µg/kg.

31. The method of claim 25 wherein the amount of the conjugate administered is 2.0 µg/kg.

32. The method of claim 25 wherein the amount of the conjugate administered is 0.5, 1.0, or 1.5 µg/kg.

33. The method of claim 25 wherein said PEG is conjugated to said alpha interferon via an epsilon amino group of a lysine residue in said alpha interferon.

34. The method of claim 25 wherein said PEG is conjugated to free amino groups of said alpha interferon via a urethane linkage.

35. The method of claim 24 wherein the conjugate is administered once per week.

36. The method of claim 24 wherein the conjugate is administered twice per week.

* * * * *

UNITED STATES PATENT AND TRADEMARK OFFICE
CERTIFICATE OF CORRECTION

PATENT NO.     : 6,524,570 B1                                                      Page 1 of 1
DATED          : February 25, 2003
INVENTOR(S)    : Paul Glue, Ph.D., David L. Cutler and Melton B. Affrime It is certified that error appears in the above-identified patent and that said Letters Patent is hereby corrected as shown below:

Title page,
Item [73], Assignee, should read -- Schering Corporation, Kenilworth, NJ (US) --.

Column 1,
Delete lines 15-23, as this is a duplicate paragraph.

Column 3,
Line 29, delete "(".
Line 31, after "-IFN" insert -- alpha --.
Line 66, after "glyco" insert -- - --.

Column 9,
Lines 11 and 13, "25" should read --24 --.

Column 10,
Lines 1, 3 and 6, "25" should read -- 24 --.

Signed and Sealed this

Eleventh Day of November, 2003

JAMES E. ROGAN
*Director of the United States Patent and Trademark Office*